(12) United States Patent
Katayama

(10) Patent No.: US 11,488,304 B2
(45) Date of Patent: Nov. 1, 2022

(54) GAUZE DETECTION SYSTEM AND GAUZE DETECTION METHOD

(71) Applicant: EIZO Corporation, Hakusan (JP)

(72) Inventor: Takuya Katayama, Kobe (JP)

(73) Assignee: EIZO Corporation, Hakusan (JP)

( * ) Notice: Subject to any disclaimer, the term of this patent is extended or adjusted under 35 U.S.C. 154(b) by 105 days.

(21) Appl. No.: 17/047,882

(22) PCT Filed: May 1, 2018

(86) PCT No.: PCT/JP2018/017431
§ 371 (c)(1),
(2) Date: Oct. 15, 2020

(87) PCT Pub. No.: WO2019/211896
PCT Pub. Date: Nov. 7, 2019

(65) Prior Publication Data
US 2021/0174499 A1    Jun. 10, 2021

(51) Int. Cl.
*G06T 7/00* (2017.01)
*G06T 7/246* (2017.01)
(Continued)

(52) U.S. Cl.
CPC ............ *G06T 7/0012* (2013.01); *A61F 13/44* (2013.01); *G06K 9/6256* (2013.01); *G06T 7/248* (2017.01);
(Continued)

(58) Field of Classification Search
CPC .......... A61B 2017/00119; G06V 20/00; G06T 2207/30242; G06T 2207/30004
See application file for complete search history.

(56) References Cited

U.S. PATENT DOCUMENTS

| | | | | |
|---|---|---|---|---|
| 5,850,465 A | * | 12/1998 | Shimura | G06V 10/44 128/920 |
| 2006/0204107 A1 | * | 9/2006 | Dugan | G06V 20/10 382/209 |

(Continued)

FOREIGN PATENT DOCUMENTS

| | | |
|---|---|---|
| JP | 3-27485 A | 2/1991 |
| JP | 5-263411 A | 10/1993 |

(Continued)

OTHER PUBLICATIONS

E. de la Fuente, F. M. Trespaderne, L. Santos, J. C. Fraile and J. P. Turiel, "Parallel computing for real time gauze detection in laparoscopy images," 2017 2nd International Conference on Bio-engineering for Smart Technologies (BioSMART), 2017, pp. 1-5, doi: 10.1109/BIOSMART.2017.8095328. (Year: 2017).*

(Continued)

*Primary Examiner* — Gandhi Thirugnanam
(74) *Attorney, Agent, or Firm* — Maier & Maier, PLLC

(57) ABSTRACT

A gauze detection system is provided that is capable of effectively detecting a gauze pad in the patient's body during surgery without applying special processing to the gauze pad. A gauze detection system 100, includes: an image input section 1 to input a taken image of an operative field; a determination section 2 to determine whether a determination target region contains a feature of a gauze image by image processing, the region having a predetermined size in an input image; and a determination result output section 3 to report detection of a gauze pad in the input image in a case of the determination target region being determined by the determination section 2 to contain the feature of the gauze image.

12 Claims, 14 Drawing Sheets

(51) Int. Cl.
*A61F 13/44* (2006.01)
*G06K 9/62* (2022.01)
*G06V 10/28* (2022.01)
*G06V 10/44* (2022.01)
*G06V 10/50* (2022.01)

(52) U.S. Cl.
CPC ............ *G06V 10/28* (2022.01); *G06V 10/457* (2022.01); *G06V 10/507* (2022.01); *G06T 2207/30004* (2013.01); *G06T 2207/30242* (2013.01); *G06V 2201/03* (2022.01)

(56) References Cited

U.S. PATENT DOCUMENTS

| | | | |
|---|---|---|---|
| 2013/0011042 A1* | 1/2013 | Satish | G06T 5/00 382/134 |
| 2014/0328517 A1* | 11/2014 | Gluncic | A61B 8/5215 382/103 |
| 2015/0221088 A1* | 8/2015 | Satish | G16Z 99/00 382/134 |
| 2016/0071264 A1* | 3/2016 | Agam | G06T 11/60 382/128 |
| 2016/0239967 A1* | 8/2016 | Chou | G06T 7/254 |
| 2016/0247275 A1* | 8/2016 | Chou | G06V 10/443 |
| 2018/0082480 A1* | 3/2018 | White | G06F 3/017 |
| 2018/0197624 A1* | 7/2018 | Robaina | G06F 3/017 |
| 2019/0038362 A1* | 2/2019 | Nash | H04N 13/366 |
| 2020/0315734 A1* | 10/2020 | El Amm | G06T 19/006 |

FOREIGN PATENT DOCUMENTS

| | | | |
|---|---|---|---|
| JP | 7-99581 A | | 4/1995 |
| JP | 8-502100 A | | 3/1996 |
| JP | 8-293025 A | | 11/1996 |
| JP | 2007-26308 A | | 2/2007 |
| JP | 2012-156839 A | | 8/2012 |
| JP | 2012-238051 A | | 12/2012 |
| JP | 2013-81557 A | | 5/2013 |
| JP | 2014-217547 A | | 11/2014 |
| JP | 2016-162130 A | | 9/2016 |
| JP | 2017042302 A | * | 3/2017 |
| JP | 2018-68863 A | | 5/2018 |
| JP | 2018068863 A | * | 5/2018 |
| WO | 2016/133767 A1 | | 8/2016 |
| WO | WO-2016133767 A1 | * | 8/2016 ............... A61B 5/06 |

OTHER PUBLICATIONS

Nilo Rivera et al., "ASSIST—Automated System for Surgical Instrument and Sponge Tracking", 2008, 2008 IEEE International Conference on RFID, The Venetian, Las Vegas, Nevada, USA, pp. 1-6 (Year: 2008).*
International Search Report dated Jul. 3, 2018 in corresponding application No. PCT/JP2018/017431; 6 pgs.
Office Action dated Sep. 11, 2020 in Japanese Patent Application No. 2016-214867 (with English translation); 13 pgs.
Office Action dated Jun. 11, 2020 in Japanese Patent Application No. 2016-214867 (with English translation); 12 pgs.

* cited by examiner

GAUZE DETECTION SYSTEM AND GAUZE DETECTION METHOD

TECHNICAL FIELD

The present invention relates to a gauze detection system and a gauze detection method that are capable of detecting a gauze pad in a patient's body by detecting a feature of a gauze image from a taken image of a situation of surgery.

BACKGROUND ART

Leaving a surgical instrument, a gauze pad, or the like in the patient's body during surgery is medical malpractice that should not occur. To prevent such leaving of a gauze pad, a gauze pad counting system is proposed in the past that confirms whether the number of gauze pads before use coincides with the number of collected gauze pads as used ones (JP 2014-217547A, described below).

In the gauze pad counting system in the past disclosed in JP 2014-217547 A, an IC tag storing gauze pad identification information is attached to each surgical gauze pad, and the number of gauze pads to be used and the number of collected gauze pads are respectively counted by a tag reader. Then, whether the number of gauze pads before use coincides with the number of collected gauze pads is confirmed to check if no gauze pads are left.

CITATION LIST

Patent Literature

PTL 1: JP 2014-217547 A

SUMMARY OF INVENTION

Technical Problem

The gauze pad counting system in the past described above has to mount an IC tag to each gauze pad and thus has problems of increasing the price of gauze pads and also taking time and effort for maintenance of the gauze pads.

It is thus an object of the present invention to provide a gauze detection system and a gauze detection method that are capable of effectively detecting gauze pads in the patient's body during surgery without applying special processing to the gauze pads.

Solution to Problem

To solve the above problems, a gauze detection system according to the present invention includes:

an image input section to input a taken image;

a determination section to determine whether a region contains a feature of a gauze image by image processing, the region having a predetermined size in an input image; and a determination result output section to report detection of a gauze pad in the input image in a case of the region being determined by the determination section to contain the feature of the gauze image.

In addition, a gauze detection method according to the present invention includes:

inputting a taken image;

determining whether a determination target region contains a feature of a gauze image by image processing, the determination target region having a predetermined size in an input image; and reporting detection of a gauze pad in the input image in a case of the region determined to contain the feature of the gauze image.

Advantageous Effects of Invention

The above configuration allows providing the gauze detection system and the gauze detection method capable of effectively detecting gauze pads in the patient's body during surgery without applying special processing to the gauze pads.

DESCRIPTION OF EMBODIMENTS

Figure 1:
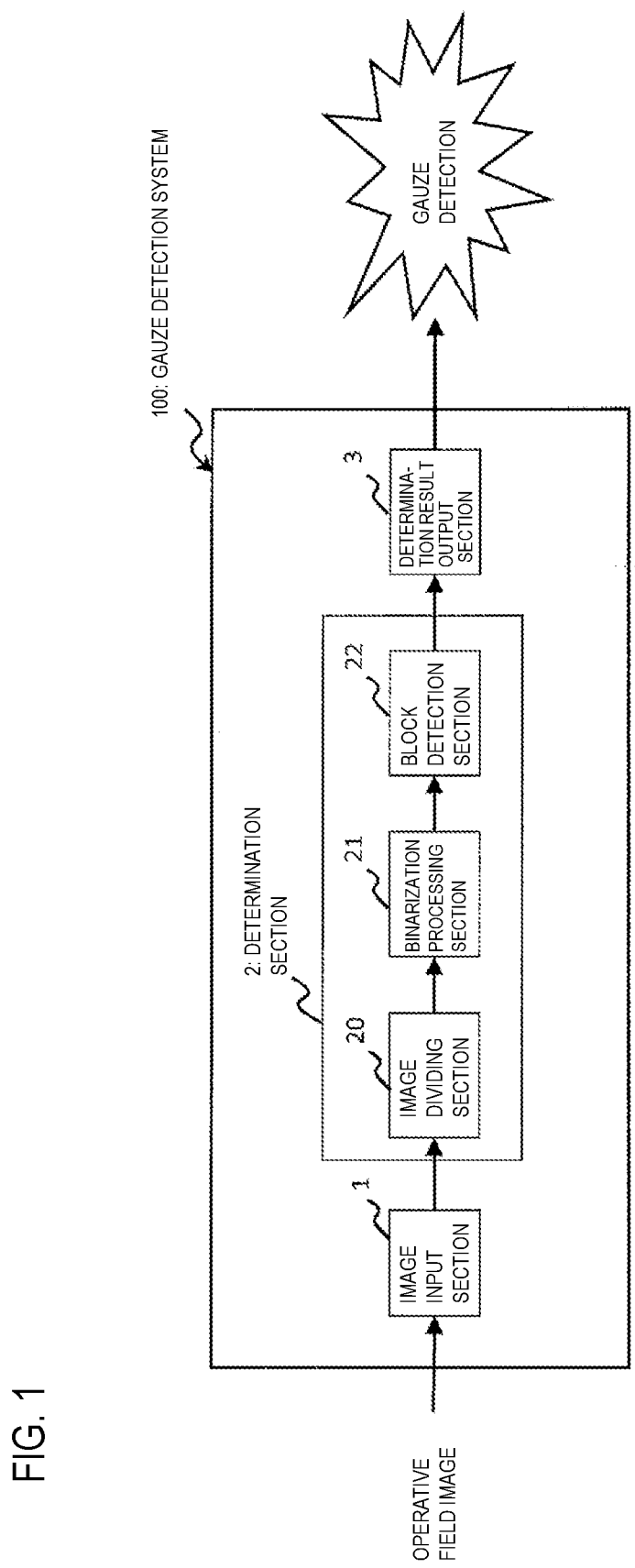
FIG. 1 is a block diagram illustrating functional schematic configuration of a gauze detection system according to a first embodiment.

A first configuration of the gauze detection system of the present invention includes:

an image input section to input a taken image;

a determination section to determine whether a determination target region contains a feature of a gauze image by image processing, the region having a predetermined size in an input image; and a determination result output section to report detection of a gauze pad in the input image in a case of the determination target region being determined by the determination section to contain the feature of the gauze image.

The above first configuration allows determination of whether the taken image of an operative field contains the feature of the gauze image by image processing and it is thus possible to effectively prevent leaving of a gauze pad without applying special processing, such as attachment of an IC tag, to a gauze pad.

In a second configuration according to the first configuration, the determination result output section includes a display control section to display, with emphasis, the determination target region determined to contain the feature of the gauze image in the taken image.

The second configuration allows emphasis display of, for example, gauze regions in the operative field image on a monitor in an operating room. This allows explicitly calling attention of an operating surgeon and assistants to the presence of a gauze pad in the operative field.

In a third configuration according to the first or second configuration, the determination section includes:

a binarization processing section to apply binarization process to the determination target region to classify each pixel as a white pixel or a black pixel; and a block detection section to detect a black pixel block with a predetermined area or less in the determination target region, and determines that the determination target region contains the feature of the gauze image when the number of the black pixel blocks detected by the block detection section is a threshold or more in the determination target region.

The third configuration allows precise determination of whether there is a gauze region in an operative field image by detecting meshes (opening areas) of a gauze pad appearing as a black pixel block in a case of applying binarization process.

In a fourth configuration according to any one of the first through third configurations, the determination section includes a brightness difference detection section to obtain a difference in brightness between adjacent pixels continued in at least one direction in the determination target region, and determines that the determination target region contains the feature of the gauze image in a case of finding a periodic change in the difference in brightness obtained by the brightness difference detection section.

Since fibers and meshes (opening areas) are regularly aligned in a gauze image, the fourth configuration allows determination of a region as a gauze region where a periodic change is found in a difference in brightness obtained between adjacent pixels continued in at least one direction in an operative field image. This allows precise determination of whether there is a gauze region in an operative field image.

In a fifth configuration according to any one of the first through fourth configurations, the determination section includes a white region detection section to detect a closed region of white pixels not continued to a boundary line of the determination target region, and determines that the determination target region does not contain the feature of the gauze image in a case of detecting the closed region by the white region detection section.

In a gauze image, a fiber area appearing as a set of white pixels in binarization is considered as a region continued to at least any of boundary lines of the determination target region and not as a closed region with the periphery surrounded by black pixels. Accordingly, in the fifth configuration, a closed region of white pixels is determined not to be the feature of the gauze image when the closed region is not continued to the boundary lines of the determination target region. This allows precise determination of whether there is a gauze region in an operative field image.

In a sixth configuration according to any one of the first through fifth configurations, the determination section includes:

a histogram generation section to generate a normalized histogram of brightness of pixels in the determination target region; and a uniformity determination section to determine that the determination target region contains the feature of the gauze image in a case of the histogram dispersed with predetermined homogeneity.

Since fiber areas and mesh areas are regularly aligned in a gauze image, a normalized histogram generated in terms of the brightness of pixels is assumed to be dispersed with predetermined homogeneity. The sixth configuration thus allows precise determination of whether there is a gauze region in an operative field image.

In a seventh configuration according to the first or second configuration, the determination section includes a neural network to learn a feature pattern of the gauze image, and determines that the determination target region contains the feature of the gauze image in a case of an image of the determination target region, the region having a predetermined size in the input image, coinciding with the feature pattern learned by the neural network.

The seventh configuration allows precise determination of whether there is a gauze region in an operative field image by sufficiently learning the feature pattern of the gauze image using an appropriate learning material.

An eighth configuration according to any one of the first through seventh configurations further includes:

a movement detection section to detect a movement direction of the region determined to contain the feature of the gauze image by the determination section in terms of a plurality of temporally continuous input images; and a counting section to count the number of gauze pads moved from outside to inside of a range of the input images and the number of gauze pads moved from inside to outside of the range of the input images based on a detection result of the movement detection section, wherein the determination result output section to report remaining gauze in a case of the number of gauze pads moved from inside to outside of the range of the input images less than the number of gauze pads moved from outside to inside of the range of the input images.

The eighth configuration allows counting entrance and exit of gauze pads relative to the operative field by detecting the movement direction of regions determined as gauze images and thus allows determination of probability (likelihood) of any gauze pad remaining in the operative field by image processing.

A computer program as a mode of the present invention is a computer readable program causing a processor of a computer to execute gauze detection process, wherein the gauze detection process includes:

image input process to input a taken image;

determination process to determine whether a determination target region contains a feature of a gauze image by image processing, the determination target region having a predetermined size in an input image; and determination result output process to report detection of a gauze pad in the input image in a case of the region determined by the determination process to contain the feature of the gauze image.

A gauze detection method according to the present invention includes:

inputting a taken image;

determining whether a determination target region contains a feature of a gauze image by image processing, the determination target region having a predetermined size in an input image; and reporting detection of a gauze pad in the input image in a case of the region determined to contain the feature of the gauze image.

Embodiments

A detailed description is given below to embodiments of the present invention with reference to the drawings. An identical reference sign is given to identical or equivalent parts in the drawings to omit repetitive descriptions. To facilitate the understanding of the description, the drawings referred below may be illustrated in a simplified or schematic configuration or may have omitted components. The scale ratio of the components illustrated in each drawing does not have to reflect the actual scale ratio.

First Embodiment

1. Overview of First Embodiment

A gauze detection system according to the first embodiment reads an image from a camera to take images of an operative field and processes the image for each frame to detect a feature of a gauze image from the taken image. As a result of the feature detection, when the probability of containing the feature of the gauze image is determined to be high, attention of the presence of gauze pad(s) in the operative field is called to an operating surgeon and assistants by displaying, with emphasis, the region representing the feature of the gauze image in the taken image and the like.

The gauze detection system may be implemented as a function of, for example, a surgery video recording and distribution system. That is, this gauze detection system may be applied to a surgery video recording and distribution system that connects a camera attached to an endoscope, an operative field camera fixed in the operating room, and the like with a server installed outside the operating room and a monitor installed in the operating room via a network to allow effective prevention of leaving a gauze pad during surgery.

2. Description on Schematic Configuration

FIG. 1 is a block diagram illustrating functional schematic configuration of a gauze detection system 100 according to the first embodiment. The block diagram illustrated in FIG. 1 conceptually illustrates the functions of the gauze detection system 100 classified into blocks and each block does not have to be actually implemented as individual hardware. Each block may be achieved by loading a predetermined program into a memory to be executed by a CPU of a server or a computer. The same applies to other block diagrams.

As illustrated in FIG. 1, the gauze detection system 100 according to the first embodiment includes: an image input section 1 to input an image of an operative field taken by a camera; a determination section 2 to determine whether a target region contains a feature of a gauze image, the region having a predetermined size in an input image; and a determination result output section 3 to call attention of the presence of gauze pad(s) in the operative field when there is a region determined to contain the feature of the gauze image by the determination section 2.

The image input section 1 inputs an image of the operative field from a camera attached to an endoscope, a fixed camera attached to, for example, an astral lamp or the like in the operating room, and the like. The operative field image is generally input as a video while it may be frame-by-frame still images. The image input section 1 extracts an image for one frame from the input image to send it to the determination section 2.

The determination section 2 divides the image for one frame received from the image input section 1 into subregions to perform image processing and determine whether the region contains the feature of the gauze image. As illustrated in FIG. 1, the determination section 2 in the present embodiment thus includes an image dividing section 20, a binarization processing section 21, and a block detection section 22.

The image dividing section 20 divides the image for one frame received from the image input section 1 into subregions to be processing units for binarization process and block detection process later in the procedure. The binarization processing section 21 applies binarization process to each subregion divided by the image dividing section 20 to classify each pixel as a white pixel or a black pixel. The block detection section 22 detects whether there is a black pixel block with a predetermined area or less in the binarized subregion. The determination section 2 determines whether the region contains the feature of the gauze image based on the number of black pixel blocks detected by the block detection section 22.

3. Description on Processing by Determination Section

Figure 2:
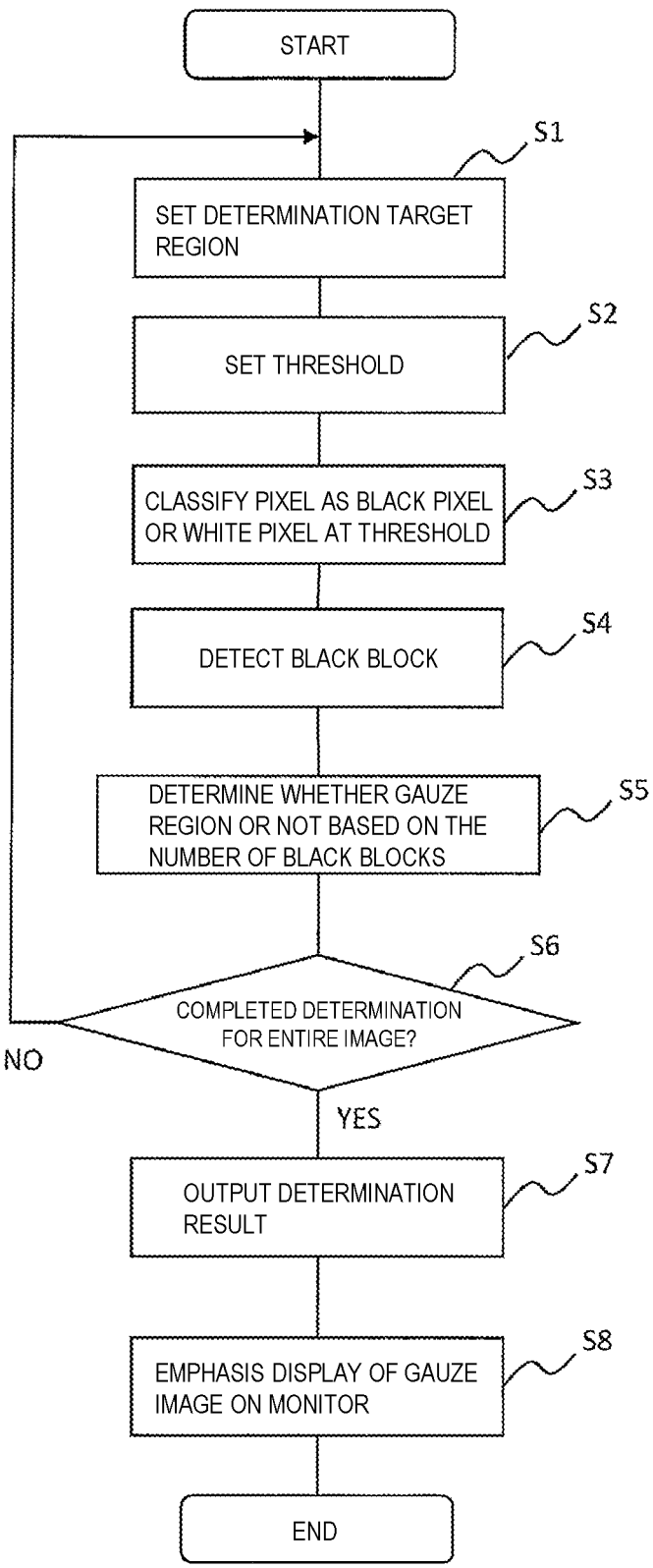
FIG. 2 is a flow chart illustrating a flow of image processing in the determination section illustrated in FIG. 1.

Here, with reference to FIG. 2, a flow of image processing by the determination section 2 is described.

At first, the image dividing section 20 divides the image for one frame received from the image input section 1 into the subregions described earlier. In other words, the image dividing section 20 sets regions having a predetermined size (generally in a rectangular shape) in the image for one frame received from the image input section 1 as regions subjected to the determination process later (determination target regions) (step S1).

Then, the binarization processing section 21 applies binarization process to all pixels contained in each determination target region set at step S1 and sets a threshold to classify each pixel as a white pixel or a black pixel (step S2). Various methods may be used as the binarization process. An example of the binarization process includes a discriminant analysis method.

Binarization by the discriminant analysis method may generally be referred to as "Otsu binarization (Otsu method)" and is a technique to obtain a threshold to maximize the resolution (ratio between the between-class variance and the within-class variance) and perform classification using the threshold thus obtained.

In this context, when the pixels in the determination target region are classified into two classes of a black pixel class and a white pixel class at a threshold of a brightness t, a within-class variance $\sigma_W^2$ may be expressed by the following equation (1) where $n_1$, $m_1$, and $\sigma_1$ denote the number of pixels, the average, and the variance of the black class, and $n_2$, $m_2$, and $\sigma_2$ denote the number of pixels, the average, and the variance of the white class.

$$\sigma_W^2 = (n_1\sigma_1^2 + n_2\sigma_2^2)/(n_1+n_2) \tag{1}$$

A between-class variance $\sigma_b^2$ may be expressed by the following equation (2) where M denotes an average of brightness values of the entire image.

$$\sigma_b^2 = \{n_1(m_1-M)^2 + n_2(m_2-M)^2\}/(n_1+n_2) \tag{2}$$

Then, the value of brightness t to maximize a resolution S, which is a ratio between the within-class variance σW2 and the between-class variance $\sigma_W^2$, is obtained to be determined as the threshold.

The binarization processing section 21 classifies the pixels in the determination target region into two of the white pixel class and the black pixel class using the brightness t thus determined as the threshold (step S3).

Then, the block detection section 22 detects a black pixel block equivalent to a "mesh area", which is one feature of the gauze image, in the determination target region (step S4). The black pixel block is a region configured with a plurality of black pixels. The black pixel block detected at step S4 is limited to one with a predetermined area or less. That is, at this step, black pixel blocks only with an area of a gauze mesh area or less are detected. The determination section 2 determines whether the determination target region is a gauze image in accordance with the number of black pixel blocks detected by the block detection section 22 (step S5).

Figure 3:
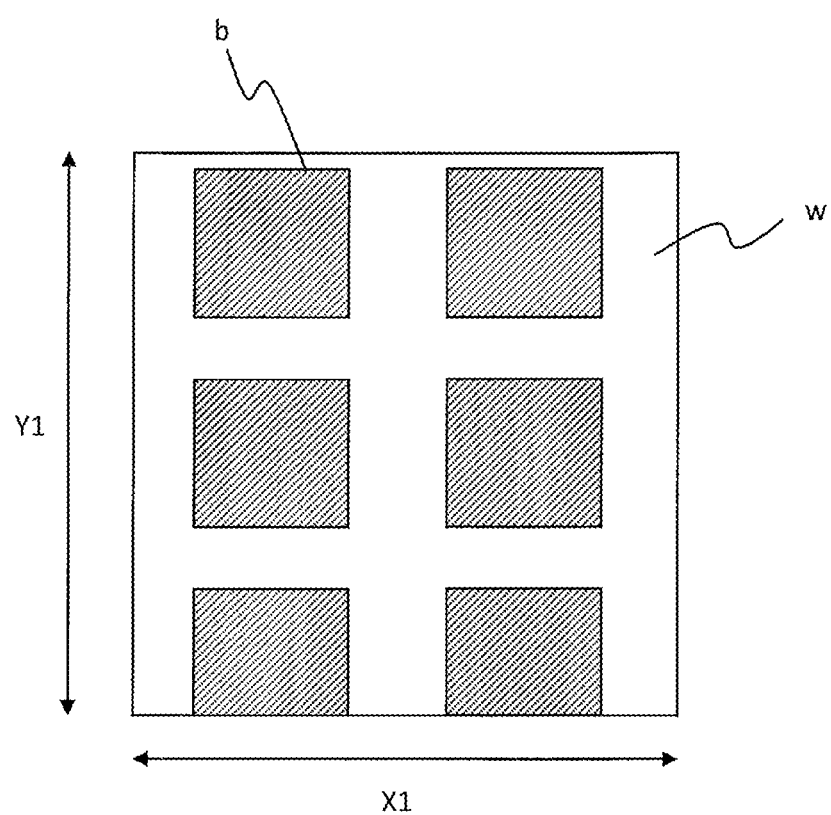
FIG. 3 is a schematic diagram illustrating an example of gauze images subjected to binarization.

As schematically illustrated in FIG. 3, in a gauze image as a binary image of black and white, a plurality of mesh areas (opening areas) b of the gauze pad in the form of black blocks are scattered in a white area w. For example, the determination section 2 thus defines each region of horizontally X1 pixels and vertically Y1 pixels as a determination target region at step S1, detects black pixel blocks with a predetermined area or less in the determination target region at step S4, and determines the determination target region as a gauze image at step S5 when a predetermined number or more of black pixel blocks are detected in the determination target region.

It should be noted that a gauze pad placed in the patient's body is bent or wrinkled, different from a state of being placed flat on a plane, and thus the meshes do not have to be in a rectangular shape as illustrated in FIG. 3. It is thus possible to precisely detect the meshes even when the meshes of the gauze pad are crushed by defining the black pixel blocks to be detected as the feature equivalent to the gauze meshes to have a predetermined area or less.

For example, when detection of five or more black pixel blocks in the determination target region determines the determination target region as a gauze image, the example illustrated in FIG. 3 is detected to have six black pixel blocks in the determination target region and thus has high probability of being determined as a gauze image.

It should be noted that the determination result by the determination section 2 may be a choice between two alternatives of "being a gauze image" and "not being a gauze image" or may be a numerical value (continuous values or discrete values) indicating the probability of being a gauze image. In the latter case, for example, thresholds in multiple stages may be provided for the number of black pixel blocks detected by the block detection section 22 in such a manner that a greater number of detected blocks causes a greater value of the probability of being a gauze image. As described later, whether the region is a gauze image may be finally determined using a factor other than the number of black pixel blocks.

The values X1 and Y1 in terms of the size of the determination target region may be arbitrarily determined considering process efficiency and the like. The area threshold of the black pixel blocks detected at step S4 to be equivalent to the mesh areas of the gauze pad may be arbitrarily determined considering the size of the meshes of the gauze pad to be used, detection precision, and the like.

After applying the process of steps S2 through S5 above to one of the determination target regions, the determination section 2 repeats the process of steps S2 through S5 by setting again a new determination target region going back to step S1 until completing the determination process for the entire input image (step S6).

When the process is completed for the entire input image (Yes at step S6), the determination section 2 outputs the results of the process to the determination result output section 3 (step S7). That is, from the determination section 2 to the determination result output section 3, data representing the determination result of whether the region is a gauze image is passed for each determination target region with the size of X1 pixels×Y1 pixels in the input image.

The determination result output section 3 generates display data to display, with emphasis, the area(s) determined as the gauze image(s) in the operative field image based on determination result data passed at step S7 and output the display data to a monitor in the operating room and the like (step S8).

Figure 4:
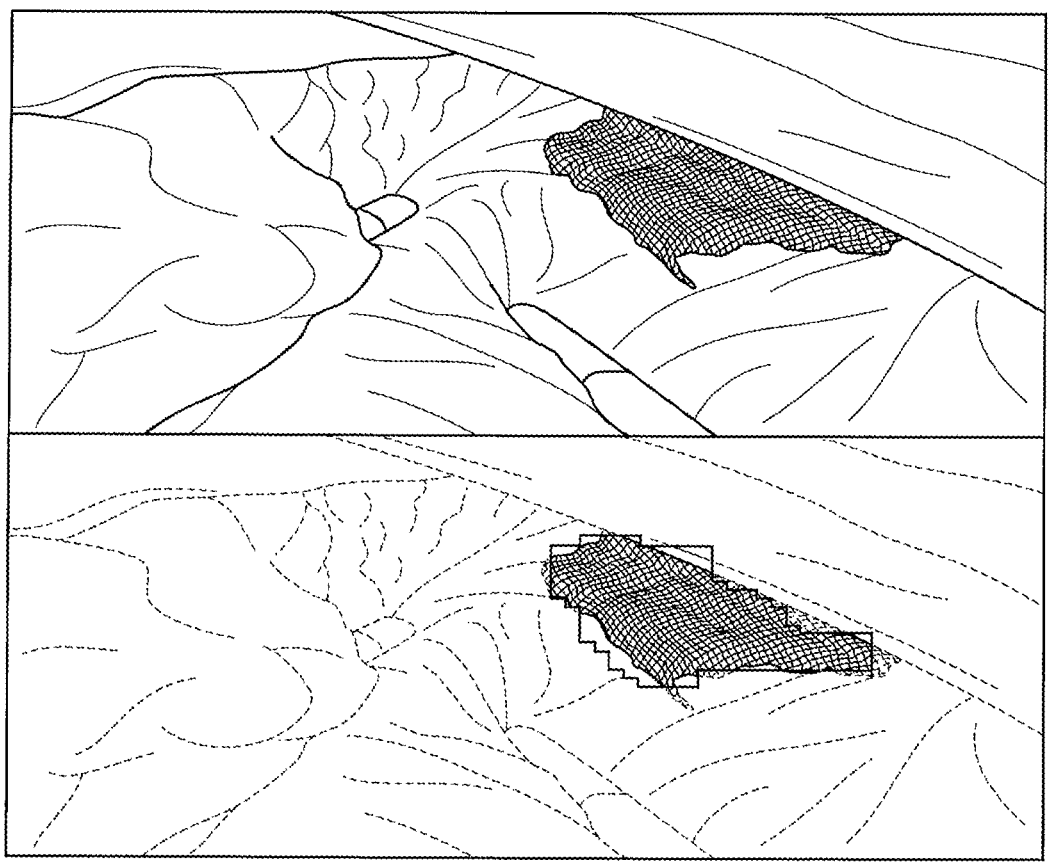
FIG. 4 is a schematic diagram illustrating an example of output to a monitor.

FIG. 4 is a schematic diagram illustrating an example of output to the monitor. In the example of FIG. 4, a monitor screen is vertically divided into two where an actual image of the operative field is displayed on an upper screen and an area determined as a gauze image in the operative field image is displayed with emphasis on a lower screen. The method of emphasis display is arbitrary and an example of the method is considered to adjust the brightness of the image so as to display the area determined as a gauze image relatively brighter and the other areas relatively darker. FIG. 4 schematically illustrates, with broken lines, the shape of the area displayed relatively darker, which is the image of internal organs and the like other than the gauze image in the operative field image. That is, the lower screen in FIG. 4 displays the area determined as a gauze image in the operative field image relatively brighter than the internal organ areas. Such emphasis display of the area determined as a gauze image allows explicitly calling attention of the presence of a gauze pad in the operative field to the operating surgeon and assistants. It should be noted that the mode of emphasis display of the gauze area is not limited to the example illustrated in FIG. 4 and may be in various modes.

5. Effects of First Embodiment

As just described, the gauze detection system 100 according to the first embodiment converts a taken image into a binarized image and determines whether there is any gauze pad in the operative field depending on whether a predetermined number or more of the meshes of the gauze pad appearing as blocks of black pixels is detected in each determination target region. Then, the area determined as a gauze image is displayed with emphasis on a monitor to call attention of the presence of the gauze pad to the operating surgeon and assistants.

This allows effective prevention of leaving a gauze pad in the patient's body only by image processing without special processing, such as attachment of an IC tag to a gauze pad.

6. Modifications

Some modifications of the gauze detection system 100 according to the present embodiment are disclosed below. The modifications below have an auxiliary assessment function to more accurately assess the presence of a gauze pad in addition to the function of assessing the presence of a gauze pad by detecting meshes of the gauze pad appearing as black pixel blocks in a binarized image.

6.1 First Modification: Assessment by Cumulative Difference of Brightness

Figure 5:
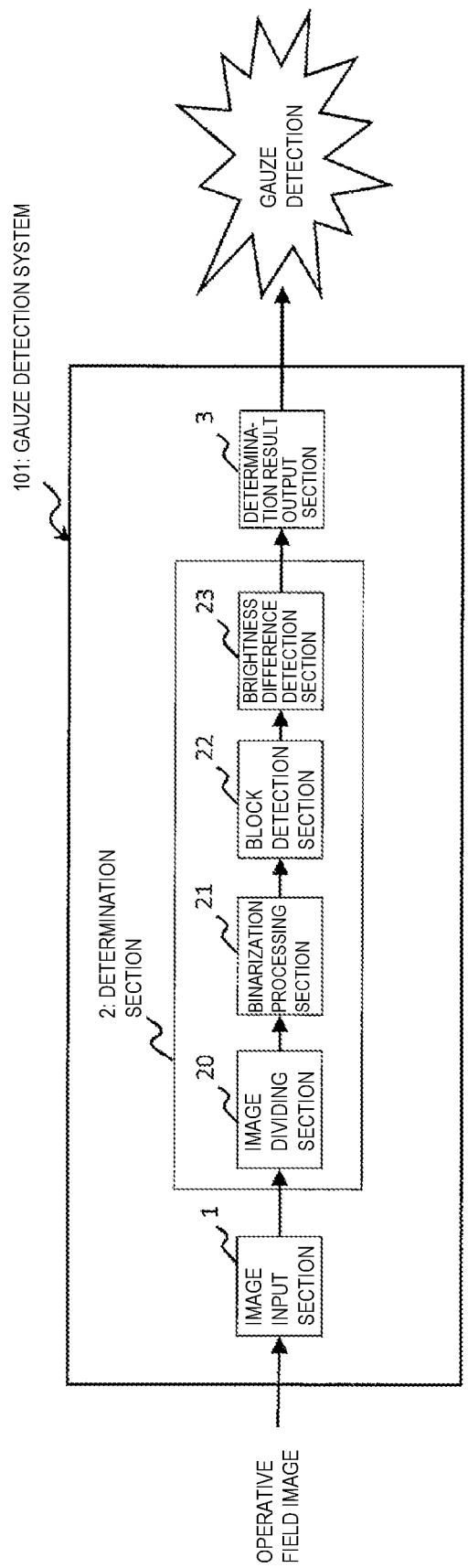
FIG. 5 is a block diagram illustrating functional schematic configuration of a gauze detection system 101 according to a first modification.

FIG. 5 is a block diagram illustrating functional schematic configuration of a gauze detection system 101 according to the first modification. As illustrated in FIG. 5, the gauze detection system 101 further includes a brightness difference detection section 23 after the block detection section 22 in the determination section 2.

The brightness difference detection section 23 detects a difference in brightness in a determination target region determined to contain the feature of the gauze image by the block detection section 22 to increase accuracy of the determination and eliminates areas that are not of the gauze image. That is, the binarization processing section 21 classifies every pixel in the determination target regions as a white pixel or a black pixel based on the threshold set by the discriminant analysis method. During this process, a mesh pattern sometimes accidentally appears in an image with a small difference in brightness (so-called flat image). The brightness difference detection section 23 is thus provided to eliminate such a determination target region with a small difference in brightness not to detect such a flat image area as the gauze image.

The brightness difference detection section 23 obtains a difference in brightness between adjacent pixels continued in at least one direction of a horizontal direction (X direction) and a vertical direction (Y direction) based on a gray scale image of the determination target region. The brightness difference detection section 23 further detects whether a change in brightness of a predetermined threshold or more is periodically observed in at least one direction of the horizontal direction (X direction) and the vertical direction (Y direction).

That is, in a gauze image, fiber areas and mesh areas periodically appear in the image plane and thus the difference in brightness between adjacent pixels appears relatively greater in the boundary area between the fibers and the meshes. Accordingly, in the determination target region containing such a gauze image, areas with a difference in brightness between adjacent pixels greater than the threshold are periodically observed when viewed in at least one direction of the horizontal direction (X direction) and the vertical direction (Y direction). In contrast, it is possible to eliminate a determination target region having no areas with a difference in brightness between adjacent pixels greater than the threshold because of high probability of containing no gauze images.

As just described, auxiliary providing the brightness difference detection section 23 to collectively determine the presence of a gauze image in addition to the processing results of the determination section 2 by detection of the gauze meshes using the black pixel blocks in the binarized image allows more secure assessment of the presence of a gauze pad in the operative field.

It should be noted that, although the brightness difference detection section 23 is provided after the block detection section 22 in the example of FIG. 5, the brightness difference detection section 23 may be provided before the binarization processing section 21 to apply later processing only to the determination target region determined to have high probability of containing a gauze image by the brightness difference detection section 23. The system may be configured to assess the presence of a gauze pad based only on the detection result of the brightness difference detection section 23. That is, the binarization processing section 21 and the block detection section 22 may be omitted to determine a determination target region with a periodically changing difference in brightness between adjacent pixels.

6.2 Second Modification: Glare Suppression

Figure 6:
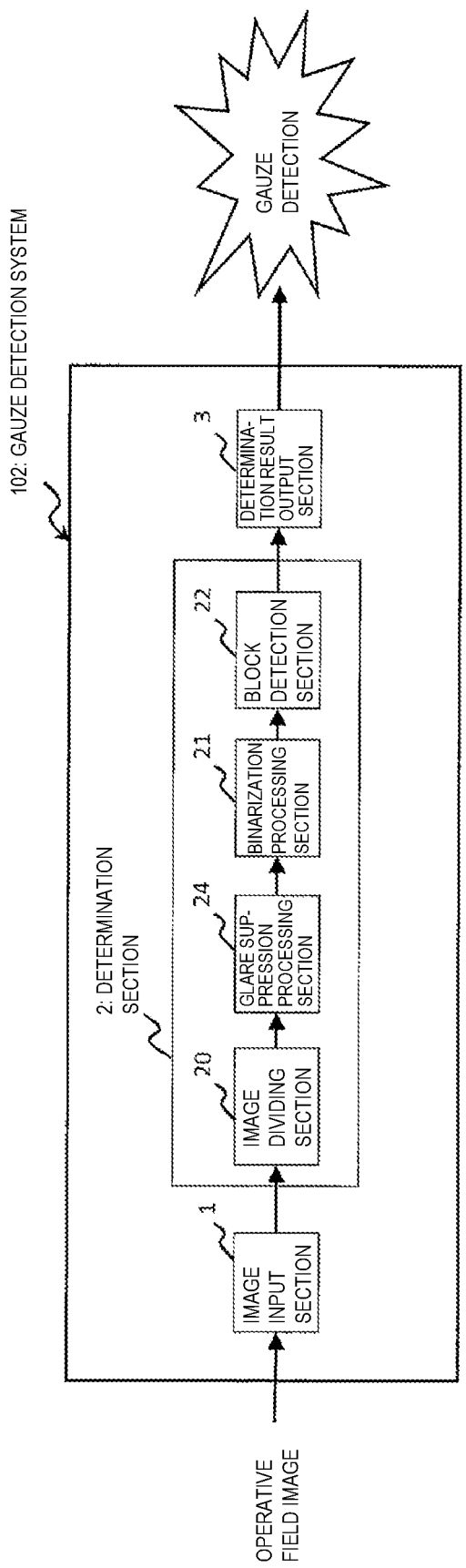
FIG. 6 is a block diagram illustrating functional schematic configuration of a gauze detection system 102 according to a second modification.

FIG. 6 is a block diagram illustrating functional schematic configuration of a gauze detection system 102 according to the second modification. As illustrated in FIG. 6, the gauze detection system 102 further includes a glare suppression processing section 24 before the binarization processing section 21 in the determination section 2.

In an operative field image, a glare is sometimes found on a surface of internal organs and the like. A glare is a state of a partial increase in brightness due to direct reflection of light. Such a glare sometimes causes accidental appearance of a mesh pattern during binarization process of the area. A glare is rarely found in gauze images. Accordingly, the areas where a glare is found are desirably eliminated from the subject of gauze image detection process assuming that they are not the gauze regions.

In addition, a glare in the image of the determination target region may cause a high brightness in the area to be noise and a risk of adversely affecting image processing of the entire determination target region. For example, when an average of the brightness in the entire determination target region is obtained, the average is sometimes calculated as a value higher than the original value due to the high brightness in the glare region. In this modification, the glare suppression processing section 24 detects such a glare region and removes the determination target region containing the glare region from the subject of the later image processing to suppress the influence of the glare.

The glare suppression processing section 24 determines a region where there are a certain number or more of pixels with higher brightness than a predetermined threshold as a glare region based on a gray scale image of the determination target region. As another example, the glare suppression processing section 24 may detect pixels with brightness higher by a threshold or more than an average brightness in the region to determine a region where there are a certain number or more of such pixels as a glare region.

As just described, the second modification further includes the glare suppression processing section 24 to eliminate a glare region from the gauze image determination target region. This allows faster gauze image detection process. It is also possible to eliminate the adverse effects of the noise by the brightness of the pixels in the glare region on the entire image processing. This allows more secure and faster detection of gauze images.

It should be noted that the glare suppression processing section 24 may be provided after the block detection section 22. However, arrangement of a processing section with relatively less computational complexity, such as the glare suppression processing section 24, earlier in the procedure allows elimination of the determination target region determined not as a gauze pad by the glare suppression processing section 24 from the subject of later processing to omit following calculation. This has an advantage of allowing faster processing in the determination section 2.

6.3 Third Modification: Assessment by Hue

Figure 7:
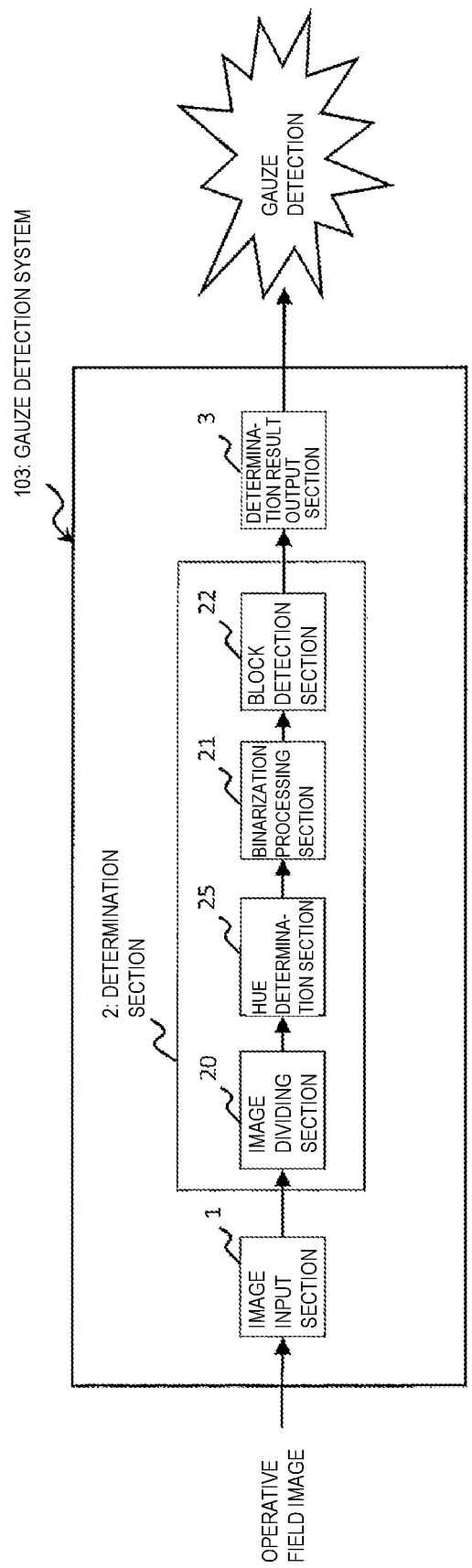
FIG. 7 is a block diagram illustrating functional schematic configuration of a gauze detection system 103 according to third modification.

FIG. 7 is a block diagram illustrating functional schematic configuration of a gauze detection system 103 according to the third modification. As illustrated in FIG. 7, the gauze detection system 103 further includes a hue determination section 25 before the binarization processing section 21 in the determination section 2. It should be noted that the hue determination section 25 may also be arranged after the block detection section 22. However, the hue determination section 25 is desirably arranged before the binarization processing section 21 from the perspective of faster processing.

The hue determination section 25 eliminates a region in a color tone clearly different from a gauze pad from the gauze image determination target region based on a color image of the determination target region. For example, fat in the body is yellowish and it is thus possible to eliminate regions in yellow from the gauze image determination target region assuming that they represent fat not a gauze pad image.

As just described, the third modification further includes the hue determination section 25 to eliminate regions in different color from the gauze pad from the gauze image determination target region. This allows faster gauze image detection process. In addition, it is possible to eliminate the adverse effects of the noise by the brightness of the pixels in the regions other than the gauze pad on the entire image processing. This allows more secure and faster detection of gauze images.

6.4 Fourth Modification: Assessment by White Region

Figure 8:
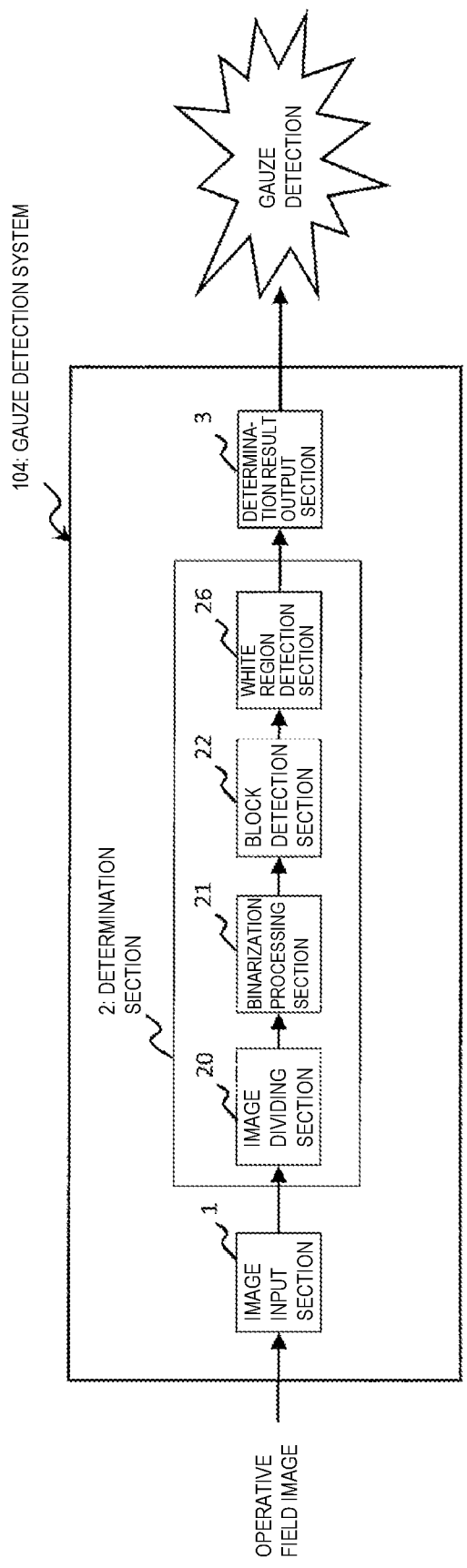
FIG. 8 is a block diagram illustrating functional schematic configuration of a gauze detection system 104 according to a fourth modification.

FIG. 8 is a block diagram illustrating functional schematic configuration of a gauze detection system 104 according to the fourth modification.

As illustrated in FIG. 8, the gauze detection system 104 is configured to include a white region detection section 26 after the block detection section 22. The white region detection section 26 determines whether there is a white region equivalent to a fiber area of a gauze pad in a region having a predetermined size in a binarized input image. In this context, the white region equivalent to a fiber area of a gauze pad is determined based on the continuity of white pixels.

Figure 9:
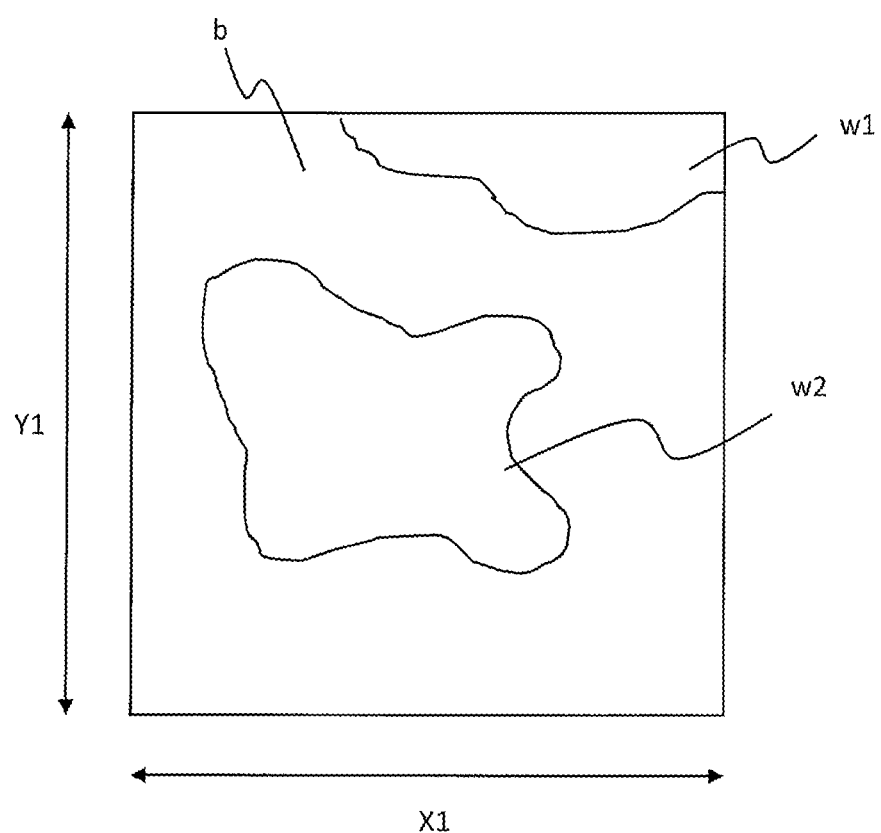
FIG. 9 is a schematic diagram illustrating an example of an image that is not a gauze image subjected to binarization.

That is, as illustrated in FIG. 3, a gauze image in the binarized input image has an area equivalent to gauze fibers appearing as a white region w. The mesh areas (opening areas) in a gauze pad appear as black regions b. The white region w equivalent to the gauze fibers is a region continued to at least any of the boundary lines of the determination target region and is not a closed region with the periphery surrounded by black pixels. That is, when there is a closed region of white pixels not continued to any boundary line of the determination target region in the determination target region, it is possible to determine the image of the determination target region not as a gauze image. For example, the example illustrated in FIG. 9 includes white regions w1 and w2 formed from white pixels, where the white region w2 is a closed region of white pixels not continued to any of the boundary lines of the determination target region. When such a closed region is contained, it is possible to determine that the image of the determination target region is not a gauze image.

Meanwhile, as in the example illustrated in FIG. 3, when the white region w continuously reaches from one boundary line of the subject of determination to another boundary line, the white region w has high probability of being a fiber area of a gauze pad.

As described above, the white region detection section 26 is capable of determining whether the image of the determination target region is a gauze image depending on whether a closed region of white pixels not continued to the boundary lines of the determination target region is detected in a binarized image. This allows an increase in precision of determination of whether each determination target region contains a gauze image by additionally applying processing by the white region detection section 26 to the determination target region determined to contain the gauze image by the block detection section 22. It should be noted that the white region detection section 26 may be arranged after the binarization processing section 21 to apply later processing only to the determination target region other than the determination target region determined not as a gauze image by the white region detection section 26.

6.5 Fifth Modification: Assessment by White Region

Figure 10:
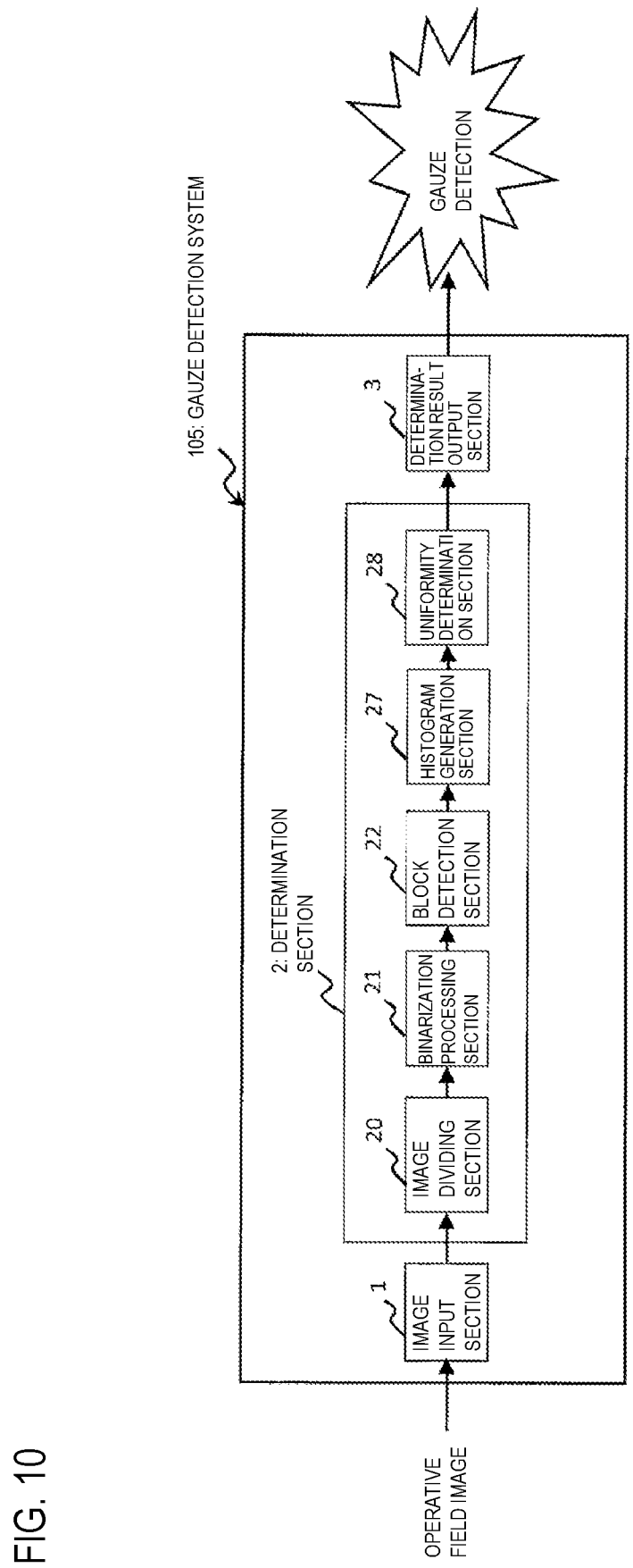
FIG. 10 is a block diagram illustrating functional schematic configuration of a gauze detection system 105 according to a fifth modification.

FIG. 10 is a block diagram illustrating functional schematic configuration of a gauze detection system 105 according to the fifth modification.

As illustrated in FIG. 10, the gauze detection system 105 is configured to include a histogram generation section 27 to generate a normalized histogram of brightness of pixels in the determination target region based on a gray scale image of the determination target region and a uniformity determination section 28 after the block detection section 22 in the determination section 2. The histogram generation section 27 and the uniformity determination section 28 apply processing to the determination target region determined to contain the feature of the gauze image by the block detection section 22, and when the histogram generated by the histogram generation section 27 is dispersed with predetermined homogeneity, the determination target region is determined to contain the feature of the gauze image. It should be noted that the histogram generation section 27 and the uniformity determination section 28 may be arranged before the binarization processing section 21.

Figure 11:
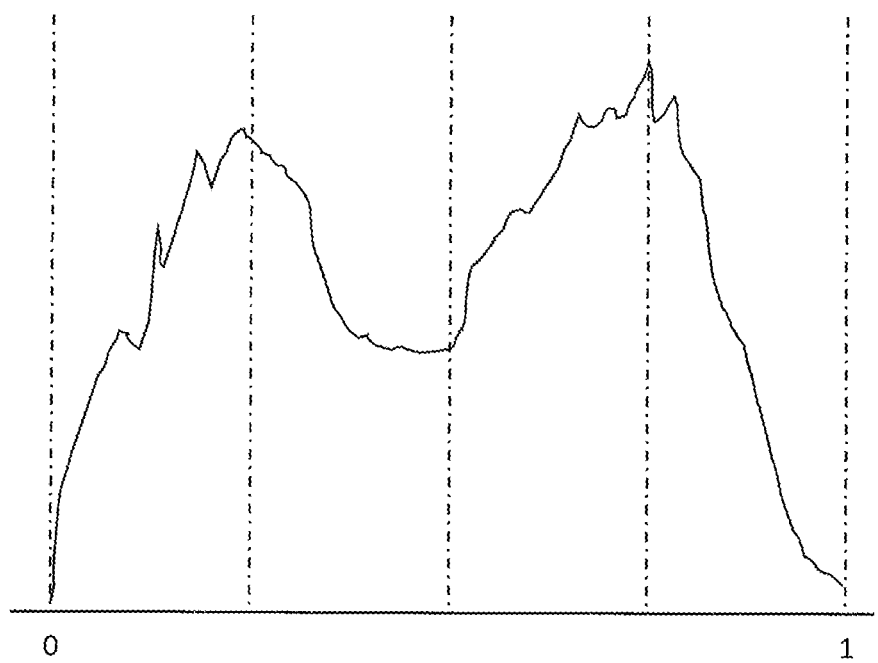
FIG. 11 is an example of a histogram of a gauze image generated in the fifth modification.

That is, since gauze fibers and meshes (opening areas) are regularly arranged in a gauze image, a brightness histogram is assumed to be ideally normalized as illustrated in FIG. 11. In the histogram of FIG. 11, the pixels contained in the determination target region has a maximum brightness of 1 and a minimum brightness of 0.

Whether "the histogram is dispersed with predetermined homogeneity" may be determined by, for example, dividing the histogram in FIG. 11 into four regions by the uniformity determination section 28 and checking whether the number (frequency) of pixels contained in each of the four regions falls within a predetermined numerical range.

As described above, the gauze detection system 105 is capable of determining whether the image of the determination target region is a gauze image using a normalized brightness histogram.

Second Embodiment

Figure 12:
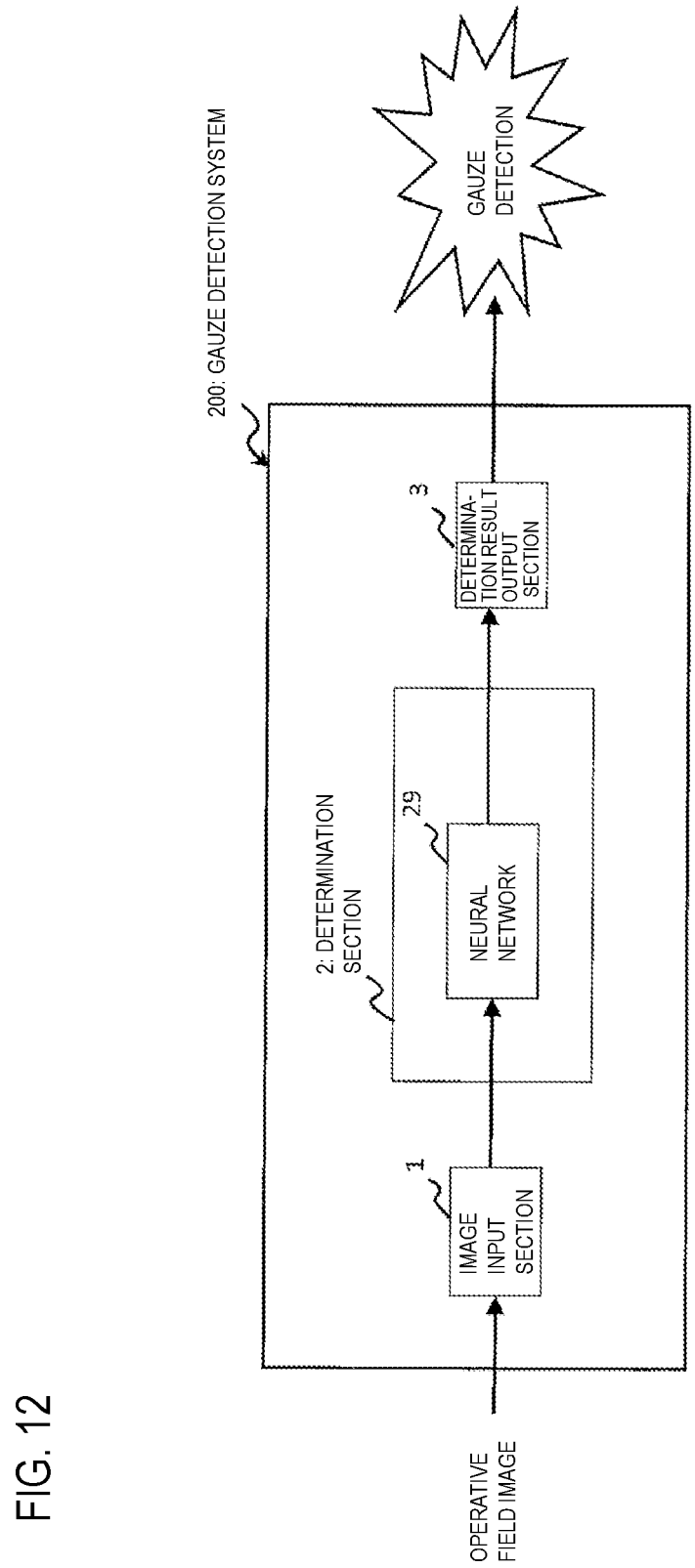
FIG. 12 is a block diagram illustrating functional schematic configuration of a gauze detection system 200 according to a second embodiment.

The second embodiment of the present invention is described below. FIG. 12 is a block diagram illustrating functional schematic configuration of a gauze detection system 200 according to the second embodiment.

As illustrated in FIG. 12, the gauze detection system 200 includes a neural network 29 to learn a feature pattern of a gauze image in the determination section 2. The technique to learn the feature pattern of the gauze image may employ an arbitrary learning technique while it is preferably a learning technique by, for example, deep learning.

For causing the neural network 29 to learn the feature pattern of the gauze image by deep learning, many images of gauze pads placed in the body during surgery are used. Use of the sufficiently learned neural network 29 allows the determination section 2 to determine that a region having a predetermined size in the input image contains the feature of the gauze image when the image of the region coincides with the feature pattern learned by the neural network 29.

As described above, the second embodiment is capable of determining whether an image of the determination target region is a gauze image using a neural network to learn the feature pattern of the gauze image.

Third Embodiment

Figure 13:
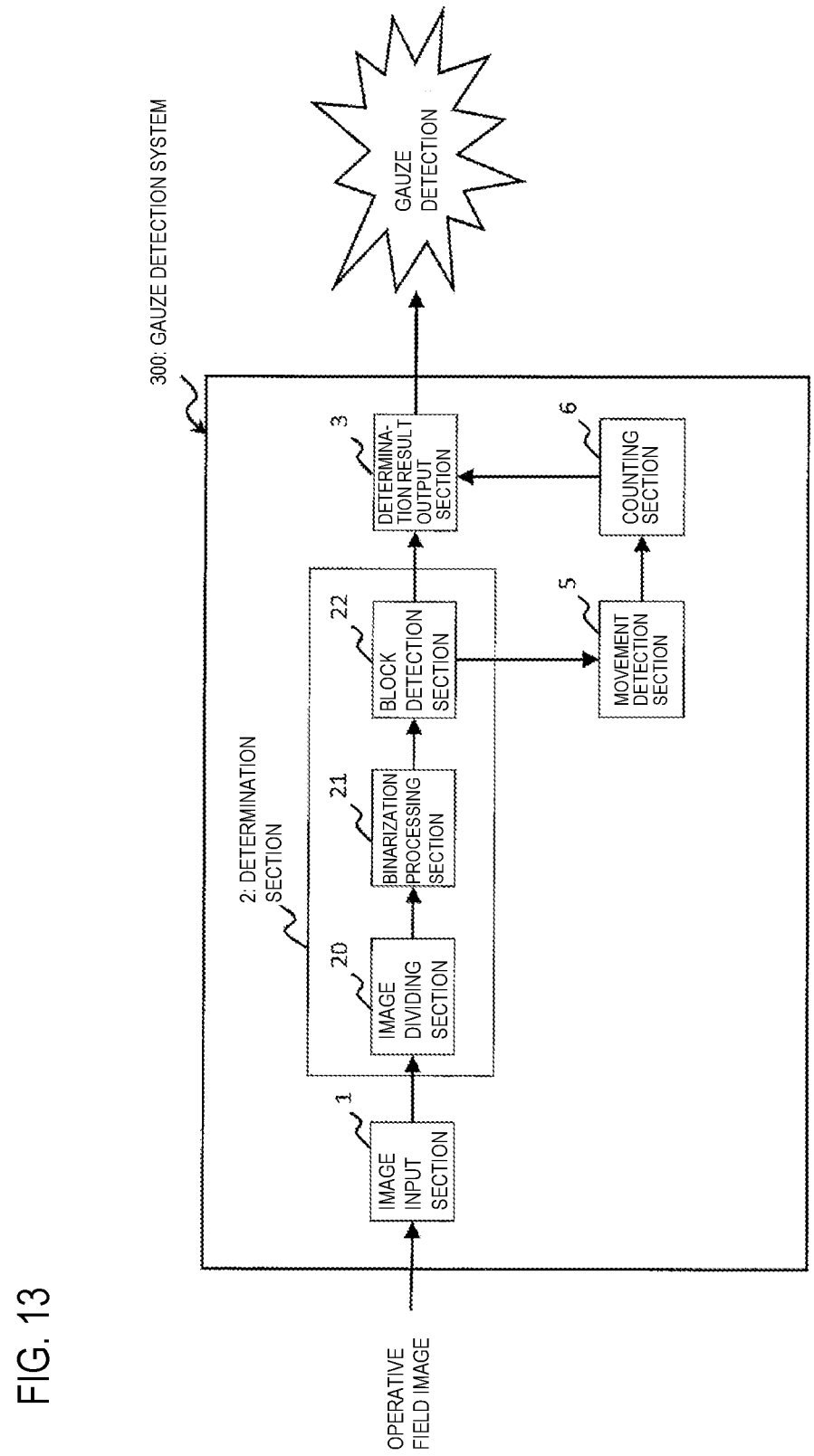
FIG. 13 is a block diagram illustrating functional schematic configuration of a gauze detection system 300 according to a third embodiment.

The third embodiment of the present invention is described below. FIG. 13 is a block diagram illustrating functional schematic configuration of a gauze detection system 300 according to the third embodiment.

As illustrated in FIG. 13, the gauze detection system 300 is different from the first embodiment in further inclusion of a movement detection section 5 and a counting section 6, in addition to the configuration described in the first embodiment, to detect entrance and exit of gauze pads relative to the operative field.

The movement detection section 5 detects movement direction of the region (gauze region) determined to contain the feature of the gauze image by the determination section 2 among a plurality of continuous frame images. The counting section 6 counts the number of gauze pads moved from outside to inside of a range of the operative field image and the number of gauze pads moved from inside to outside of the range of the operative field image based on the detection result of the movement detection section 5.

Figure 14:
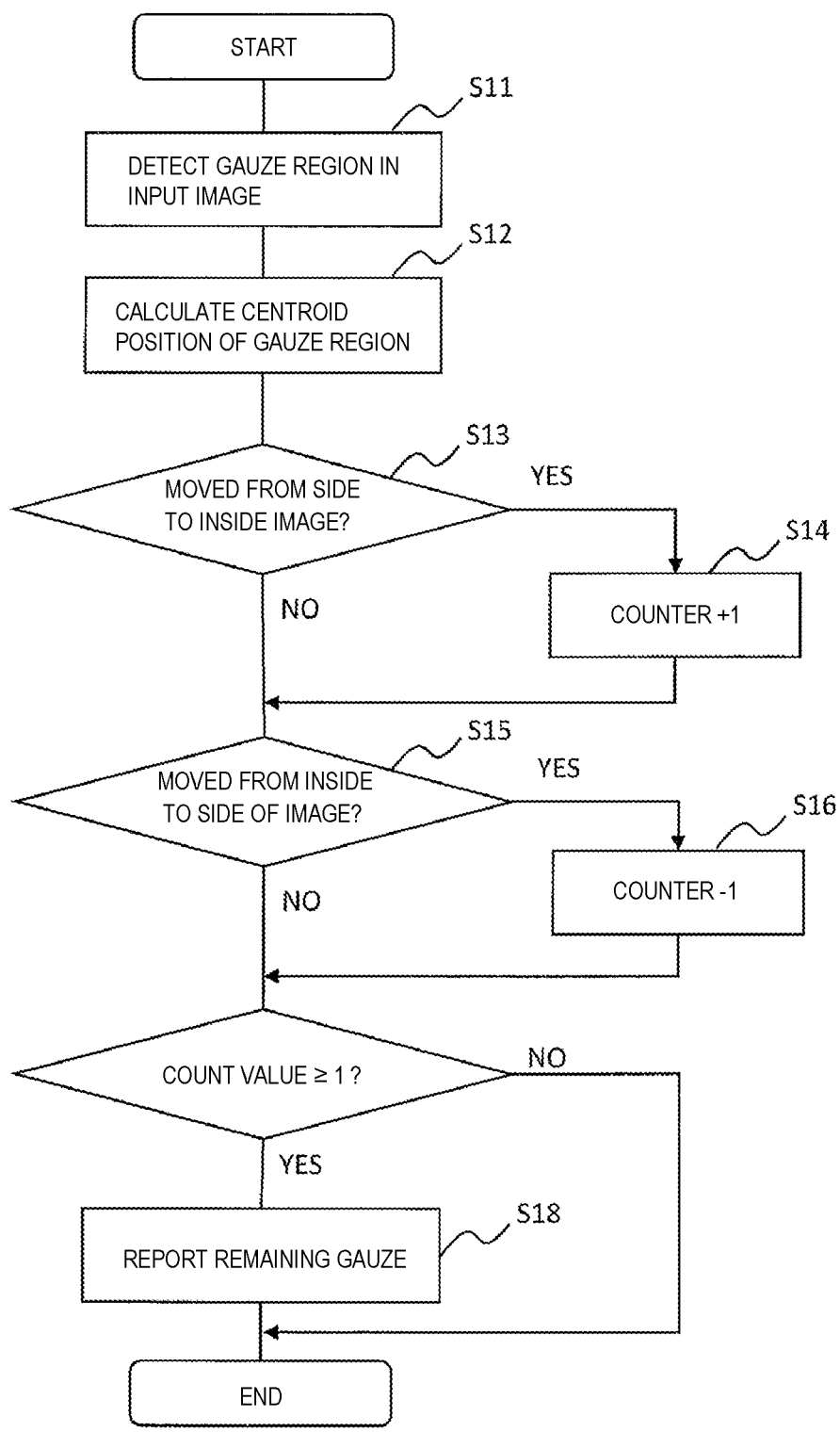
FIG. 14 is a flow chart illustrating a process flow of detecting entrance and exit of gauze pads in the gauze detection system 300.

FIG. 14 is a flow chart illustrating a process flow of detecting entrance and exit of gauze pads in the gauze detection system 300.

Step S11 in FIG. 14 is equivalent to the processing at steps S1 through S6 (determination process by the determination section 2) described in the first embodiment. That is, an input image of one frame is divided into determination target regions having a predetermined size and whether each region contains the feature of the gauze image is determined for all determination target regions to detect gauze regions in the input image. Then, the movement detection section 5 obtains the centroid position of the region determined to contain the feature of the gauze image in the operative field image (step S12).

When an image of a next frame is input, the process goes back to step S11 to determine whether the input image of the next frame contains the feature of the gauze image, and similar to above, obtain the centroid position of the region determined to contain the feature of the gauze image for the image of this frame (step S12).

Repeating the process at steps S11 and S12 allows finding out the direction of moving the centroid position of the region determined to contain the feature of the gauze image over the plurality of continuous frames.

When, in one frame, the centroid position of a gauze region appears near any of the four sides of the operative field image and is moved inside the image in the following frame (Yes at step S13), a new gauze pad is assumed to be fed and the number of gauze pad count is incremented by 1 (step S14).

On the contrary, when the centroid position of a gauze region is moved from inside the operative field image to any of the four sides of the image over the continuous frames and then disappears (Yes at step S15), a gauze pad is assumed to be taken out of the operative field and the number of gauze pad count is decremented by 1 (step S16).

When a region containing the feature of the gauze image suddenly disappears without movement of the centroid position to any of the four sides of the image, a gauze pad is highly probably hidden in the shadow of an internal organ or a surgical instrument or buried under the blood.

Accordingly, it is possible to accurately recognize entrance and exit of gauze pads in the operative field by detecting both the movement direction of the centroid position of a gauze region and the relationship between the centroid position and the four sides of the image over the plurality of continuous frames.

Then, at the time of completing the surgery, if the number of gauze pads moved from inside to outside of the range of the operative field image is less than the number of gauze pads moved from outside to inside of the range of the operative field image, that is, the number of gauze pad count at the time of completing the surgery is one or more (Yes at step S17), the determination result output section 3 reports that the gauze pad(s) remains in the operative field (step S18).

As described above, in the third embodiment, the number of gauze pads entered the operative field and the number of gauze pads taken out of the operative field are counted by obtaining the centroid position of the gauze region and the movement direction of the centroid position over the plurality of frames. When the number of gauze pads entered the operative field does not coincide with the number of gauze pads taken out of the operative field, attention is called to the operating surgeon and assistants by, for example, displaying the situation on a monitor. This allows effective prevention of leaving a gauze pad without applying special processing, such as an IC tag, to the gauze pad.

FIG. 13 exemplifies a configuration of adding the movement detection section 5 and the counting section 6 to the configuration (gauze detection system 100) in the first embodiment. It should be noted that the present embodiment may be configured to add the movement detection section 5 and the counting section 6 to any of the configurations (gauze detection systems 101 through 105) described as modifications of the first embodiment or the configuration (gauze detection system 200) in the second embodiment.

Although some embodiments of the present invention have been described, embodiments of the present invention are not limited only to the above specific examples and may be variously modified. It is also possible to carry out the present invention by appropriately combining the functions described the respective embodiments and modifications.

For example, in the above embodiments, an example of using the discriminant analysis method as a specific example of the binarization process. However, as described earlier, the technique of binarization process is not limited to this and may use other techniques. Other examples of the binarization process include, but not limited to, adaptive binarization process and the like. Binarization process relative to a predetermined (fixed) threshold that is appropriately set may be used as well.

In the above description, the embodiments of the gauze detection system are described as a computer system implemented in a server or a computer. It should be noted that a mode of carrying out the present invention contains a computer program and a storage medium storing the same to achieve the functions of the respective blocks described above on a general-purpose server or computer.

All or part of the processing of each functional block in the above embodiments may be achieved by a program. All or part of the processing of each functional block in the above embodiments is executed by a central processing unit (CPU) in a computer. The program to perform respective processing is stored in a storage device, such as a hard disk and a ROM, and executed in the ROM or by loaded into a RAM.

The respective processing in the above embodiments may be achieved by hardware or may be achieved by software (including the cases of achieved together with an operating system (OS), middleware, or a predetermined library). It may be achieved by process in combination of software and hardware.

The order to execute the processing method in the above embodiments is not limited to the description of the above embodiments and the order of execution is allowed to be changed without departing from the spirit of the invention.

The scope of the present invention includes a computer program causing a computer to execute the method described earlier and a computer readable storage medium having the program stored therein. Examples of the computer readable storage medium include flexible disks, hard disks, CD-ROMs, MOs, DVDs, DVD-ROMs, DVD-RAMs, Blu-ray discs (BD), and semiconductor memories.

The computer program is not limited to those stored in the above storage medium and may be transmitted via electrical communication lines, wireless or wired communication lines, networks including the internet, and the like.

REFERENCE SIGNS LIST

1: Image Input Section, 2: Determination Section, 3: Determination Result Output Section, 5: Movement Detection Section, 6: Counting Section, 20: Image Dividing Section, 21: Binarization Processing Section, 22: Block Detection Section, 23: Brightness Difference Detection Section, 24: Glare Suppression Processing Section, 25: Hue Determination Section, 26: White Region Detection Section, 27: Histogram Generation Section, 28: Uniformity Determination Section, 29: Neural Network, 100-105, 200, 300: Gauze Detection System

The invention claimed is:

1. A gauze detection system, comprising:
an image input section to input a taken image;
a determination section to determine whether a determination target region contains a feature of a gauze image by image processing, the region having a predetermined size in an input image; and
a determination result output section to report detection of a gauze pad in the input image in a case of the determination target region being determined by the determination section to contain the feature of the gauze image, wherein
the determination section includes:
a binarization processing section to apply binarization process to the determination target region to classify each pixel as a white pixel or a black pixel; and
a block detection section to detect a black pixel block with a predetermined area or less in the determination target region, and
the determination section determines that the determination target region contains the feature of the gauze image when the number of the black pixel blocks detected by the block detection section is a threshold or more in the determination target region.

2. The gauze detection system according to claim 1, wherein the determination result output section includes a display control section to display, with emphasis, the determination target region determined to contain the feature of the gauze image in the taken image.

3. The gauze detection system according to claim 1, wherein the determination section further comprises
a brightness difference detection section to obtain a difference in brightness between adjacent pixels continued in at least one direction in the determination target region, and
determines that the determination target region contains the feature of the gauze image in a case of finding a periodic change in the difference in brightness obtained by the brightness difference detection section.

4. The gauze detection system according to claim 1, wherein the determination section further comprises
a white region detection section to detect a closed region of white pixels not continued to a boundary line of the determination target region, and
determines that the determination target region does not contain the feature of the gauze image in a case of detecting the closed region by the white region detection section.

5. The gauze detection system according to claim 1, wherein the determination section further comprises:
a histogram generation section to generate a normalized histogram of brightness of pixels in the determination target region; and
a uniformity determination section to determine that the determination target region contains the feature of the gauze image in a case of the histogram dispersed with predetermined homogeneity.

6. The gauze detection system according to claim 1, further comprising:
a movement detection section to detect a movement direction of the region determined to contain the feature of the gauze image by the determination section in terms of a plurality of temporally continuous input images; and
a counting section to count the number of gauze pads moved from outside to inside of a range of the input images and the number of gauze pads moved from inside to outside of the range of the input images based on a detection result of the movement detection section, wherein
the determination result output section to report remaining gauze in a case of the number of gauze pads moved from inside to outside of the range of the input images less than the number of gauze pads moved from outside to inside of the range of the input images.

7. A non-transitory computer readable storage medium storing a computer readable program causing a processor of a computer to execute gauze detection process, wherein the gauze detection process comprises:
image input process to input a taken image;
determination process to determine whether a determination target region contains a feature of a gauze image by image processing, the determination target region having a predetermined size in an input image; and
determination result output process to report detection of a gauze pad in the input image in a case of the region determined by the determination process to contain the feature of the gauze image, wherein
the determination process includes:
binarizing the determination target region to classify each pixel as a white pixel or a black pixel;
detecting a black pixel block with a predetermined area or less in the determination target region; and
determining that the determination target region contains the feature of the gauze image when the number of the black pixel blocks is a threshold or more in the determination target region.

8. A gauze detection method, comprising:
inputting a taken image;
determining whether a determination target region contains a feature of a gauze image by image processing, the determination target region having a predetermined size in an input image; and
reporting detection of a gauze pad in the input image in a case of the region determined to contain the feature of the gauze image, wherein determining whether the determination target region contains the feature of the gauze image includes:

binarizing the determination target region to classify each pixel as a white pixel or a black pixel;

detecting a black pixel block with a predetermined area or less in the determination target region; and determining that the determination target region contains the feature of the gauze image when the number of the black pixel blocks is a threshold or more in the determination target region.

9. A gauze detection system, comprising:

an image input section to input a taken image;

a determination section to determine whether a determination target region contains a feature of a gauze image by image processing, the region having a predetermined size in an input image; and a determination result output section to report detection of a gauze pad in the input image in a case of the determination target region being determined by the determination section to contain the feature of the gauze image, wherein the determination section includes:

a binarization processing section to apply binarization process to the determination target region to classify each pixel as a white pixel or a black pixel; and a white region detection section to detect a closed region of white pixels not continued to a boundary line of the determination target region, and determines that the determination target region does not contain the feature of the gauze image in a case of detecting the closed region by the white region detection section.

10. The gauze detection system according to claim 9, wherein the determination result output section includes a display control section to display, with emphasis, the determination target region determined to contain the feature of the gauze image in the taken image.

11. A non-transitory computer readable storage medium storing a computer readable program causing a processor of a computer to execute gauze detection process, wherein the gauze detection process includes:

image input process to input a taken image;

determination process to determine whether a determination target region contains a feature of a gauze image by image processing, the determination target region having a predetermined size in an input image; and determination result output process to report detection of a gauze pad in the input image in a case of the region determined by the determination process to contain the feature of the gauze image, wherein the determination process includes:

binarizing the determination target region to classify each pixel as a white pixel or a black pixel;

detecting a closed region of white pixels not continued to a boundary line of the determination target region, and determining that the determination target region does not contain the feature of the gauze image in a case of detecting the closed region by the white region detection section.

12. A gauze detection method, comprising:

inputting a taken image;

determining whether a determination target region contains a feature of a gauze image by image processing, the determination target region having a predetermined size in an input image; and reporting detection of a gauze pad in the input image in a case of the region determined to contain the feature of the gauze image, wherein determining whether the determination target region contains the feature of the gauze image includes:

binarizing the determination target region to classify each pixel as a white pixel or a black pixel;

detecting a closed region of white pixels not continued to a boundary line of the determination target region, and determining that the determination target region does not contain the feature of the gauze image in a case of detecting the closed region by the white region detection section.

* * * * *